United States Patent
Wang et al.

(10) Patent No.: US 8,766,192 B2
(45) Date of Patent: Jul. 1, 2014

(54) METHOD FOR INSPECTING A PHOTOVOLTAIC SUBSTRATE

(75) Inventors: Ran Shi Wang, Kwai Chung (HK); Jiangwen Deng, Kwai Chung (HK); Chung Yan Lau, Kwai Chung (HK)

(73) Assignee: ASM Assembly Automation Ltd, Hong Kong (HK)

( * ) Notice: Subject to any disclaimer, the term of this patent is extended or adjusted under 35 U.S.C. 154(b) by 912 days.

(21) Appl. No.: 12/916,694

(22) Filed: Nov. 1, 2010

(65) Prior Publication Data

US 2012/0104255 A1    May 3, 2012

(51) Int. Cl.
*G01J 5/02*    (2006.01)

(52) U.S. Cl.
USPC .................................. 250/341.1; 250/341.4

(58) Field of Classification Search
USPC .......................................... 250/341.1, 341.4
See application file for complete search history.

(56) References Cited

U.S. PATENT DOCUMENTS

| | | | |
|---|---|---|---|
| 4,988,875 A * | 1/1991 | Ortiz et al. | 250/330 |
| 2005/0231713 A1* | 10/2005 | Owen et al. | 356/237.1 |
| 2005/0252545 A1 | 11/2005 | Nowlan et al. | |
| 2011/0123091 A1* | 5/2011 | Janssens et al. | 382/145 |
| 2012/0307236 A1* | 12/2012 | Ortner et al. | 356/239.3 |

FOREIGN PATENT DOCUMENTS

| | | |
|---|---|---|
| CN | 101762611 A | 6/2010 |
| JP | 2010-54377 A | 3/2010 |

* cited by examiner

*Primary Examiner* — David Porta
*Assistant Examiner* — Mindy Vu
(74) *Attorney, Agent, or Firm* — Ostrolenk Faber LLP

(57) ABSTRACT

A method for inspecting a substrate having intrinsic heterogeneous patterns for the presence of cracks comprises the steps of providing an optical device and front-side lighting on a first side of the substrate and providing near-infrared lighting on a second side of the substrate opposite to the first side. The near-infrared lighting is operable to penetrate the substrate so as to be detectable by the optical device through the substrate. One or more images are obtained by illuminating the substrate with the front-side lighting and/or the near-infrared lighting from the second side. The one or more images are thereafter processed to distinguish between the heterogeneous patterns on the substrate and any cracks present on the substrate.

9 Claims, 6 Drawing Sheets

METHOD FOR INSPECTING A PHOTOVOLTAIC SUBSTRATE

FIELD OF THE INVENTION

The invention relates to the inspection of a substrate having intrinsic heterogeneous patterns, and in particular, to the inspection of such a substrate to search for cracks on the substrate.

BACKGROUND AND PRIOR ART

For high-throughput and low-cost production, the thickness of solar wafers consisting of photovoltaic elements has been reduced to 200 μm or below. Thinner substrates give rise to lower wafer stability and a higher risk of wafer breakage. An effective method to detect cracks and even micro-cracks is therefore important in order to reject those wafers that have a higher potential to fail.

Some approaches to detecting the presence of micro-cracks which rely on non-visual inspection include the use of ultrasonic energy, thermal energy or heating, thermosonic energy and mechanical flexing. Furthermore, there are visual approaches such as Electroluminescence (EL) inspection and Photoluminescence (PL) inspection, which are two popular visual methods. Electroluminescence inspection requires electrical contact and then can only be used in a finished solar cell. Photoluminescence requires a uniform illumination source with appropriate non-uniformity correction, and the shot-to-shot reproducibility is usually poor.

US Patent Publication number 2005/0252545 A1 entitled "Infrared Detection of Solar Cell Defects under Forward Bias" discloses a cell inspection system which applies a forward-bias current to cause heating. The resulting thermal image of applies a forward-bias current to cause heating. The resulting thermal image of each cell is then analyzed with an infrared camera to inspect the cell for cracks. However, this approach is relatively expensive and slow.

Apart from the above approaches, a purely visual approach has also been adopted in the prior art, although it is generally less accurate. Since silicon is semitransparent in the near-infrared (NIR) spectrum, NIR backlight inspection is widely used for incoming raw solar wafer but suffers from various disadvantages. For instance, a polycrystalline material on the substrate typically displays intrinsic heterogeneous features, and some features have patterns that are similar to a micro-crack pattern. Hence, it is difficult to distinguish a micro-crack from the general surface texture. Moreover, the camera resolution needs to be very high in order to distinguish a micro-crack. Even if a camera that is capable of achieving up to 8,000×8,000 pixels-per-substrate is used, the pixel resolution is still only 20 μm. This is far below the resolution required for detecting micro-cracks.

To illustrate the above shortcoming, FIG. 1 is a side view of a conventional inspection system 100 using near-infrared ("NIR") backlighting 106 to detect cracks on a substrate 102. Homogeneous NIR backlighting 106 from a single light source is projected from underneath a substrate 102 such as a photovoltaic element. The light from the NIR backlighting 106 penetrates the substrate 102 where a micro-crack 104 is present, towards an imaging optical device 108. The imaging optical device 108 then transmits the light to an image grabbing sensor 110.

FIG. 2 is a photograph showing an image of a substrate 102 that has been illuminated with NIR backlighting 106 using the conventional inspection system 100. The substrate 102 has multiple heterogeneous features due to its polycrystalline grain textures. Some of these features have patterns that are similar to a micro-crack pattern, and it is difficult for the conventional inspection system 100 to discern the presence of a micro-crack 102. It would be advantageous to develop a method and system for identifying micro-cracks on substrates having such intrinsic heterogeneous features more effectively and accurately.

SUMMARY OF THE INVENTION

It is thus an object of the invention to seek to provide visual means to detect micro-cracks on a photovoltaic substrate which avoids the above shortcomings of the prior art.

According to a first aspect of the invention, there is provided a method for inspecting a substrate having intrinsic heterogeneous patterns, comprising the steps of: providing an optical device and front-side lighting on a first side of the substrate; providing near-infrared lighting on a second side of the substrate opposite to the first side, the near-infrared lighting being operable to penetrate the substrate so as to be detectable by the optical device through the substrate; obtaining a first image of the substrate illuminated by the front-side lighting; obtaining a second image of the substrate illuminated by the near-infrared lighting from the second side; and thereafter processing the first and second images to distinguish between the heterogeneous patterns on the substrate and any cracks present on the substrate.

According to a second aspect of the invention, there is provided a method for inspecting a substrate having intrinsic heterogeneous patterns, comprising the steps of: providing an optical device and front-side lighting on a first side of the substrate; providing near-infrared lighting on a second side of the substrate opposite to the first side, the near-infrared lighting being operable to penetrate the substrate so as to be detectable by the optical device through the substrate; obtaining an image of the substrate illuminated by both the front-side lighting and the near-infrared lighting simultaneously; and thereafter processing the image of the substrate to distinguish between the heterogeneous patterns on the substrate and any cracks present on the substrate.

It will be convenient to hereinafter describe the invention in greater detail by reference to the accompanying drawings, which illustrate one embodiment of the invention. The particularity of the drawings and the related description is not to be understood as superseding the generality of the broad identification of the invention as defined by the claims.

DETAILED DESCRIPTION OF THE PREFERRED EMBODIMENT OF THE INVENTION

Figure 1:
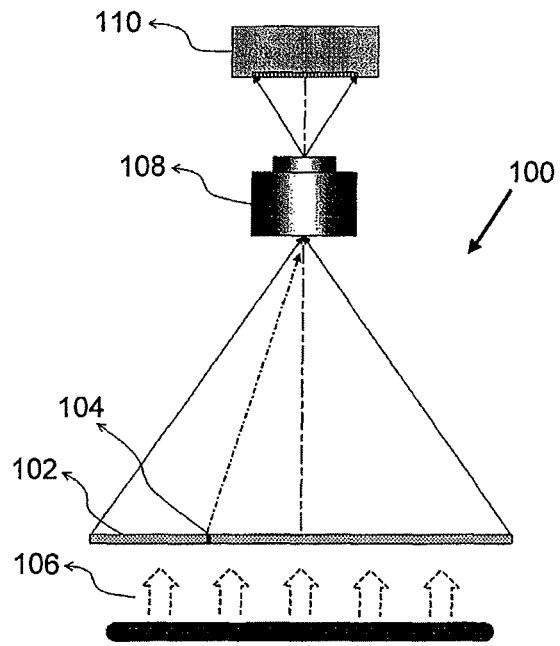
FIG. 1 is a side view of a conventional inspection system using NIR backlighting to detect cracks on a substrate.
Figure 2:
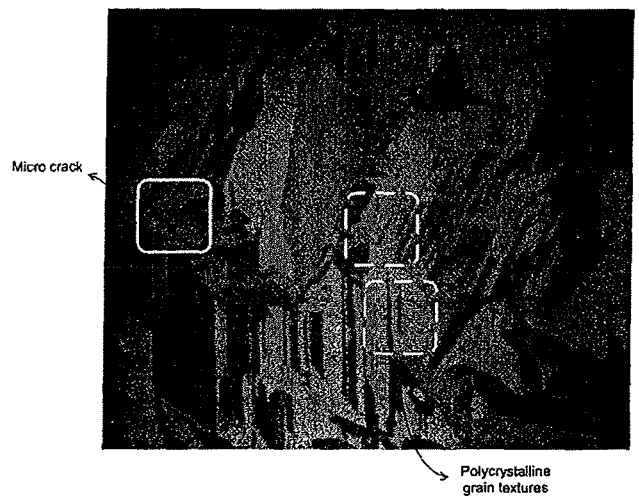
FIG. 2 is a photograph showing an image of the substrate that has been illuminated with NIR backlighting using the conventional inspection system.
Figure 3:
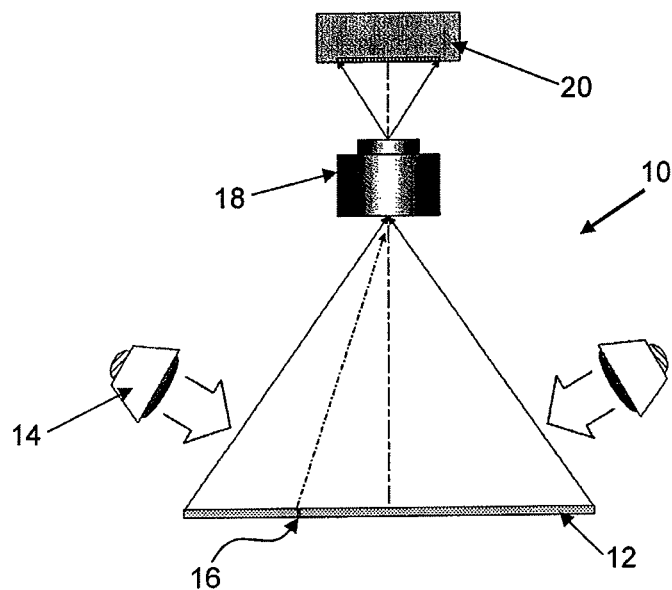
FIG. 3 is a side view of an inspection system comprising front-side lighting for detecting cracks on a substrate according to a first preferred embodiment of the invention.

FIG. 3 is a side view of an inspection system 10 comprising front-side lighting 14 for detecting cracks 16 on a substrate 12 having intrinsic heterogeneous patterns according to a first preferred embodiment of the invention. The front-side lighting 14 comprises a plurality of front-side light sources on a first or top side of the substrate 12, which are preferably arranged at different positions surrounding the substrate 12. They are preferably also inclined at oblique angles with respect to a plane of the substrate 12 for illuminating a top surface of the substrate 12, most preferably at an angle of less than 40° relative to the plane of the substrate 12. The reflected light is directed towards an imaging optical device 18 and transmitted to an optical device in the form of an image grabbing sensor 20.

With the multiple light sources from the front-side lighting 14 illuminating the substrate 12, the grain contrast of the substrate 12 is highlighted. Alternatively, the grain boundaries of the substrate 12 can be highlighted by grabbing multiple images generated by the respective light sources of the front-side lighting 14. In this case, multiple images of the substrate 12 are obtained while the substrate 12 is illuminated by the front-side lighting 14, wherein each image of the substrate 12 is obtained while it is illuminated by a respective one of the plurality of front-side light sources.

Figure 4:
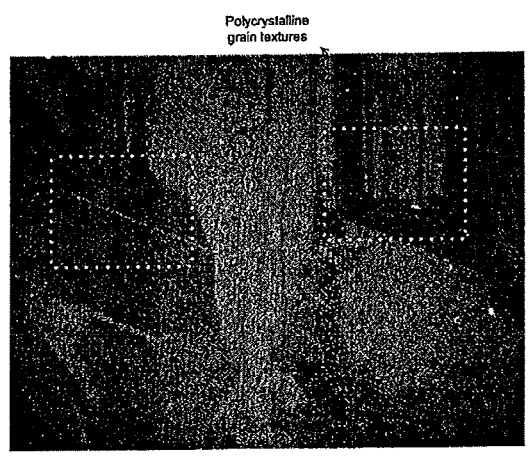
FIG. 4 is a photograph showing an image of a substrate that has been illuminated with front-side lighting using the inspection system of FIG. 3.

FIG. 4 is a photograph showing an image of a substrate that has been illuminated with front-side lighting 14 using the inspection system of FIG. 3. The image is used to increase the photovoltaic grain contrast and to highlight grain boundaries on the substrate 12. This helps to determine the polycrystalline grain texture boundaries during further processing of the image.

Figure 5:
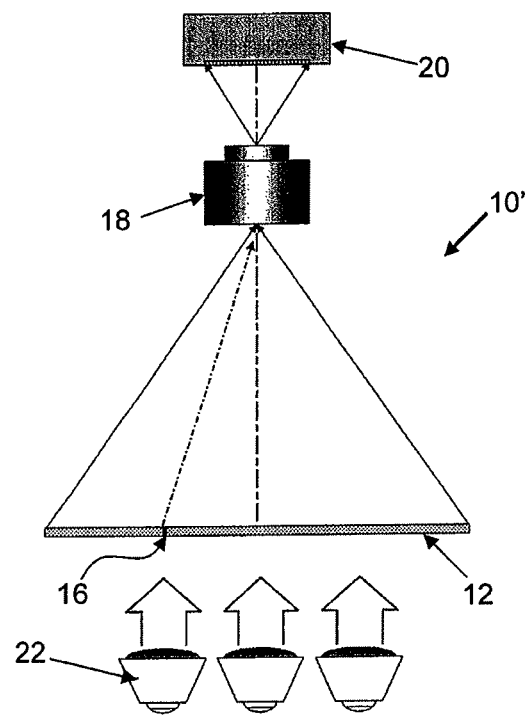
FIG. 5 is a side view of an inspection system comprising NIR backlighting for detecting cracks on a substrate according to the first preferred embodiment of the invention.

FIG. 5 is a side view of an inspection system 10' comprising NIR backlighting 22 for detecting cracks 16 on a substrate 12 on a second or bottom side of the substrate 12 according to the first preferred embodiment of the invention. There are preferably multiple NIR backlighting 22 light sources arranged at different positions surrounding the substrate 12, as opposed to the single homogeneous backlighting source used in the prior art. By directing NIR backlighting 22 from various angles against the micro-crack 16, the shadow of the micro-crack 16 is enlarged and rendered visually more distinct.

Figure 10:
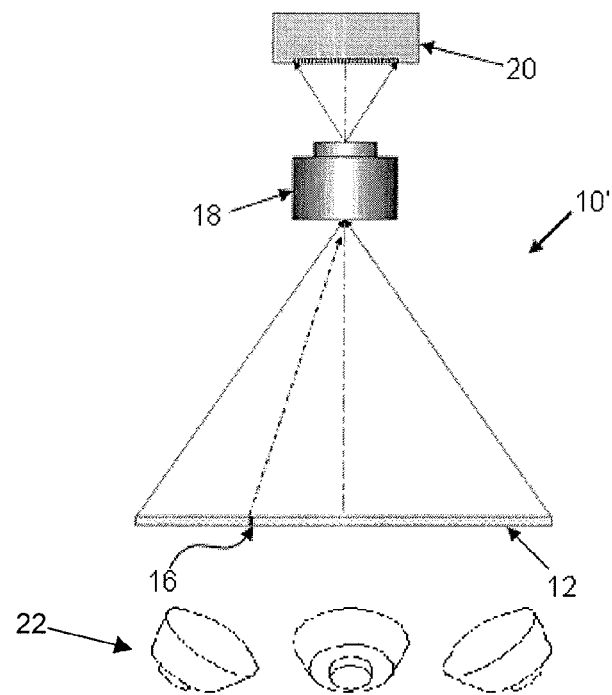
FIG. 10 is a side view of an inspection system comprising NIR backlighting illustrating, by way of example, positioning of the light sources according to an aspect of the disclosure.
Figure 11:
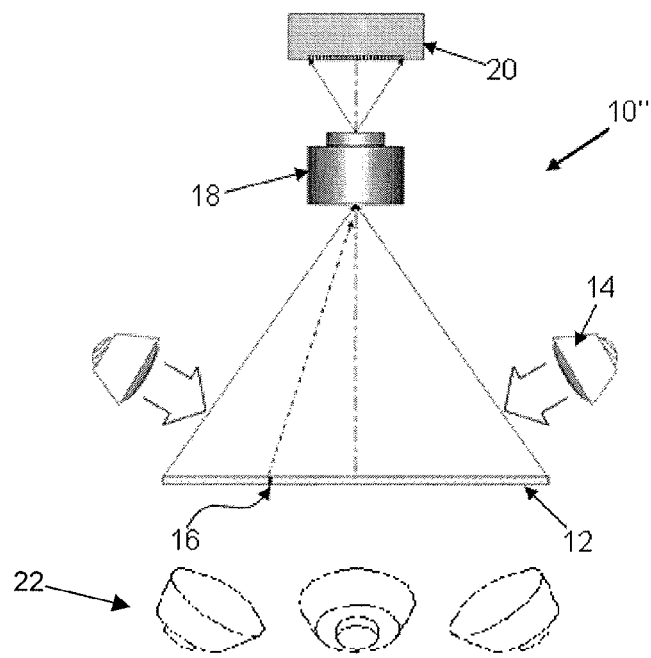
FIG. 11 is a side view of an inspection system comprising a combination of front-side lighting and NIR backlighting, illustrating positioning of the backlighting light sources, according to an example of an embodiment according to the present disclosure.

The NIR backlighting 22 light sources are preferably inclined at oblique angles relative to the plane of the substrate 12, and are also equally-spaced with respect to one another. Most preferably, there are three NIR backlighting 22 light sources that are arranged at 120° with respect to one another. FIGS. 10 and 11 show examples of various types of positioning of the NIR backlighting 22 light sources, which, by way of example, are illustrated as three in number.

Figure 6:
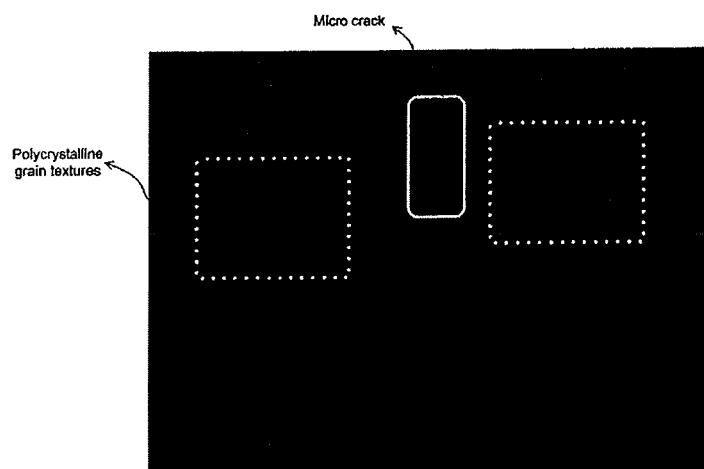
FIG. 6 is a photograph showing an image of a substrate that has been illuminated with NIR backlighting using the inspection system of FIG. 5.

The NIR backlighting 22 is operable to penetrate the substrate 12 so as to be detectable by the imaging optical device 18 and image grabbing sensor 20 through the substrate 12. FIG. 6 is a photograph showing an image of a substrate that has been illuminated with NIR backlighting 22 using the inspection system 10' of FIG. 5. Although the image obtained from backlighting is relatively darker as compared to the image in FIG. 4 obtained from front-side illumination, the advantage is that both the grain boundaries on the substrate 12 and the micro-crack 16 are highlighted.

Where first and second images, $I_{front}$ and $I_{back}$, are grabbed separately using the respective front-side lighting 14 and NIR backlighting 22 as described above, the composite image can be processed using compensation, generally by using the following formula:

$$I = w_1 \cdot I_{back} + w_2 \cdot I_{front}$$

with proper weightage given to $w_1$ and $w_2$.

In essence, the first image $I_{front}$ highlights pattern boundaries by providing increased grain contrast, whereas the second image $I_{back}$ highlights the pattern boundaries at an inverse phase to that produced in the first image $I_{front}$, including any cracks on the substrate 12. Using the above algorithm, it is possible to distinguish between the heterogeneous patterns on the substrate 12 and any cracks, in particular micro-cracks 16, present on the substrate 12.

If the front-side lighting 14 and NIR backlighting 22 are not precisely controlled or are not uniform enough, the compensation could further be processed sequentially for each potential crack detected in $I_{back}$ which is illuminated by NIR backlighting 22. In one example, images of the substrate 12 can be obtained while the substrate 12 is illuminated by a respective one of the plurality of NIR backlighting 22 light sources.

Alternatively, it is possible to grab just one image simultaneously provided that there is precise control of the intensity of the front-side lighting 14 and NIR backlighting 22 such that they are proportional. With proper control of the respective intensities, any cracks on the image are highlighted while the pattern boundaries on the substrate 12 are obscured due to cancellation or compensation of the different phases of images of the grain boundaries produced by the front-side lighting 14 and NIR backlighting 22 respectively.

Figure 7:
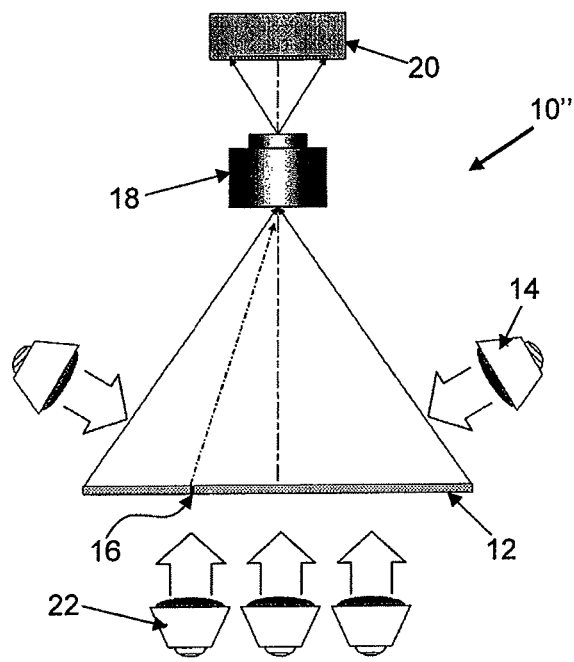
FIG. 7 is a side view of an inspection system comprising a combination of simultaneous front-side lighting and NIR backlighting for detecting cracks on a substrate according to a second preferred embodiment of the invention.

FIG. 7 is a side view of an inspection system 10" comprising a combination of simultaneous front-side lighting 14 and NIR backlighting 22 for detecting cracks 16 on a substrate 12. An image of the substrate 12 that is obtained while the substrate 12 is illuminated by both the front-side lighting 14 and the NIR backlighting 22 at the same time is grabbed. The image is then processed in order to identify the micro-crack 16 more accurately.

Figure 8:
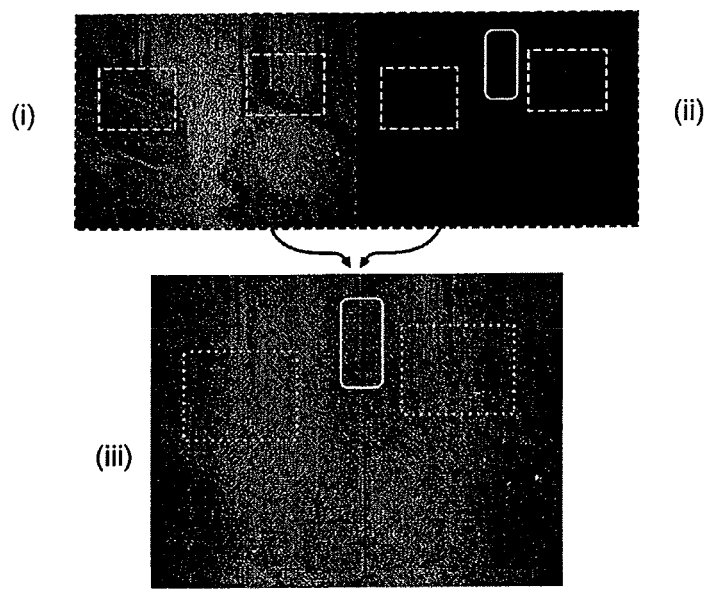
FIG. 8 are photographs showing images of a substrate that has been illuminated with (i) front-side lighting and (ii) near-infrared backlighting, as well as (iii) a combined image obtained from simultaneous front-side lighting and near-infrared backlighting.

An explanation how a single image distinctively showing the micro-crack is obtained can be explained by way of FIG. 8, which are photographs showing images of a substrate that has been illuminated with (i) front-side lighting and (ii) near-infrared backlighting, as well as (iii) a processed image obtained from simultaneous front-side lighting 14 and NIR backlighting 22.

The grain contrast of the polycrystalline grain textures on the substrate 12 is reduced by reflectivity compensation of the front-side lighting 14, based on the fact that the inter-grain intensity contrasts by front-side and NIR backlighting are in reversed phases. As an exemplary illustration, FIG. 8(i) shows the grain reflectivity difference under the front-side lighting 14, and FIG. 8(ii) separately shows the grain difference through the NIR backlighting 22.

Figure 9:
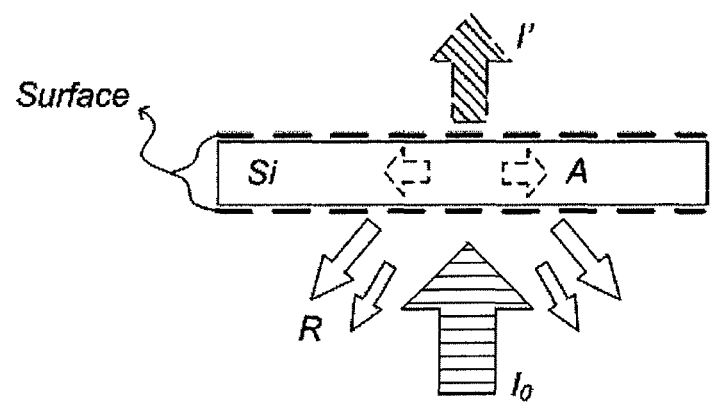
FIG. 9 is a schematic diagram demonstrating optical transmission characteristics of a silicon substrate at the NIR wavelength band.

FIG. 9 is a schematic diagram demonstrating optical transmission characteristics of a silicon substrate at the NIR wavelength band. The observed distinct grain texture contrasts between front-side and back-side lighting is due to the special optical characteristic of the substrate material, in this case silicon, at the NIR wavelength band. The transmitted light intensity I' (which can be observed by the vision system) will be proportional to an incident beam intensity $I_0$, which experiences two main types of losses, namely integrated surface reflection and absorption by bulk material. The relationship can be expressed by the equation:

$$I'=(1-A)\cdot(1-R)\cdot I_0 \quad \text{(Equation 1)}$$

where R refers to the overall reflection effect from the dual surfaces, and A is the absorption effect from material of the silicon substrate.

Therefore, the potential causes to texture contrast on a polycrystalline silicon substrate under backlighting conditions may come from two sources: the absorption difference and the reflection difference among grains. However, for a typical NIR backlighting condition for solar wafer substrate applications (e.g. lighting having 1050 nm wavelength and a 200 μm silicon substrate), A is much smaller than R and the value of A is negligible. Thus, Equation 1 can be further simplified as:

$$I'=(1-R)\cdot I_0 \quad \text{(Equation 2)}$$

Consequently, it can be concluded that the grain texture contrast on a polycrystalline wafer under NIR backlighting is dominated by the inter-grain reflectance difference. The texture contrast from the front-side lighting, which is proportional to R, should be inversely correlated to texture contrast from NIR backlighting. That enables grain texture contrast compensation by the combination of front-side lighting and NIR backlighting, with appropriate weighting offered for effective micro-crack detection on a polycrystalline solar wafer substrate.

A few assumptions are made in relation to the above analysis. For example in most conditions, the distribution of grain textures is assumed to be highly aligned on both sides of the polycrystalline wafer. This assumption relies on the fact that the observable grain must have sufficiently large dimensions (e.g. greater than 0.3 mm) relative to the thickness of the substrate when it is cut into a very thin slice (e.g. generally less than 0.3 mm).

It is further assumed that the grain contrast is primarily caused by a difference in reflectivity instead of by transmission. Thus, whilst the dark area in FIG. 8(ii) is caused by a relatively higher reflective area on the back surface as observed through the back-side lighting, the same area will appear bright under the front-side lighting 14 (see FIG. 8(i)). The brightness in relation to such area is caused by a relatively higher reflective area on the front surface. With front-side lighting 14 and NIR backlighting 22 switched on simultaneously and proportionally, the reflectivity compensation result is as shown in FIG. 8(iii). It would be noted that the grain contrast is significantly reduced and the micro-crack 16 appears more prominently.

However, one shortcoming of the second preferred embodiment is that there is a strict duality requirement in that the front-side lighting 14 and NIR backlighting 22 must be precisely controlled. On the other hand, by processing the two images which have been obtained separately according to the first preferred embodiment of the invention, this strict duality requirement for one image grabbed by simultaneous front-side lighting 14 and NIR backlighting 22 can be avoided.

The invention described herein is susceptible to variations, modifications and/or additions other than those specifically described and it is to be understood that the invention includes all such variations, modifications and/or additions which fall within the spirit and scope of the above description.

The invention claimed is:

1. A method of inspecting a substrate having intrinsic heterogeneous patterns, the method comprising the steps of:
providing an optical device and front-side lighting on a first side of the substrate;
providing near-infrared lighting on a second side of the substrate opposite to the first side, the near-infrared lighting comprising a plurality of near-infrared light sources and operable to penetrate the substrate so as to be detectable by the optical device through the substrate;
obtaining at least one first image of the substrate illuminated by the front-side lighting;
obtaining a plurality of second images of the substrate illuminated by the near-infrared lighting from the second side, wherein each image of the substrate is obtained while the substrate is illuminated by a respective one of the plurality of near-infrared light sources; and thereafter
processing the first and second images to distinguish between the heterogeneous patterns on the substrate and any cracks present on the substrate.

2. The method as claimed in claim 1, wherein the front-side lighting comprises a plurality of front-side light sources, the front-side light sources being arranged at different positions surrounding the substrate and inclined at oblique angles relative to a plane of the substrate.

3. The method as claimed in claim 2, further comprising:
the step of obtaining multiple images of the substrate while the substrate is illuminated by the frontside lighting,
wherein each image of the substrate is obtained while it is illuminated by a respective one of the plurality of front-side light sources.

4. The method as claimed in claim 2, wherein the front-side light sources are inclined at less than 40° relative to the plane of the substrate.

5. The method as claimed in claim 1, wherein light sources of the plurality of near-infrared light sources are arranged at positions different from one another and surrounding the substrate, and are each positioned and inclined at an oblique angle relative to a plane of the substrate.

6. The method as claimed in claim 5, wherein the light sources of the plurality of near-infrared light sources are equally-spaced with respect to one another.

7. The method as claimed in claim 5, wherein the near-infrared lighting comprises three near-infrared light sources that are arranged at an angle of 1200 with respect to one another.

8. The method as claimed in claim 1, wherein the front-side lighting is operative to increase grain contrast and to highlight pattern boundaries on the first image of the substrate.

9. The method as claimed in claim 8, wherein the near-infrared lighting is operative to highlight the pattern boundaries at an inverse phase to that produced by the front-side lighting on the second image of the substrate and any cracks on the substrate.

* * * * *